(12) United States Patent
Yu

(10) Patent No.: US 11,413,428 B2
(45) Date of Patent: *Aug. 16, 2022

(54) CATHETER INSERTION SYSTEM AND METHOD OF FABRICATION

(71) Applicant: Auris Health, Inc., Redwood City, CA (US)

(72) Inventor: Alan Yu, Union City, CA (US)

(73) Assignee: Auris Health, Inc., Redwood City, CA (US)

(*) Notice: Subject to any disclaimer, the term of this patent is extended or adjusted under 35 U.S.C. 154(b) by 513 days.

This patent is subject to a terminal disclaimer.

(21) Appl. No.: 16/452,393

(22) Filed: Jun. 25, 2019

(65) Prior Publication Data

US 2019/0307987 A1    Oct. 10, 2019

Related U.S. Application Data

(63) Continuation of application No. 13/832,352, filed on Mar. 15, 2013, now Pat. No. 10,376,672.

(51) Int. Cl.
| | | |
|---|---|---|
| *A61M 25/01* | (2006.01) | |
| *A61B 1/00* | (2006.01) | |
| *A61B 34/30* | (2016.01) | |

(52) U.S. Cl.
CPC ....... *A61M 25/0105* (2013.01); *A61B 1/0016* (2013.01); *A61B 1/00133* (2013.01); *A61B 34/30* (2016.02); *A61B 2034/301* (2016.02)

(58) Field of Classification Search
CPC .......... A61M 25/0105; A61M 25/0147; A61M 2025/015; A61B 1/00133; A61B 1/0016; A61B 34/30; A61B 2034/301; A61B 2017/003; A61B 34/37

See application file for complete search history.

(56) References Cited

U.S. PATENT DOCUMENTS

| | | | |
|---|---|---|---|
| 3,572,325 A | 3/1971 | Bazell et al. | |
| 3,913,565 A | 10/1975 | Kawahara | |
| 4,294,234 A | 10/1981 | Matsuo | |
| 4,392,485 A | 7/1983 | Hiltebrandt | |
| 4,607,619 A | 8/1986 | Seike et al. | |
| 4,690,175 A | 9/1987 | Ouchi et al. | |
| 4,706,656 A | 11/1987 | Kuboto | |
| 4,741,326 A | 5/1988 | Sidall et al. | |

(Continued)

FOREIGN PATENT DOCUMENTS

| | | |
|---|---|---|
| CN | 1846181 | 10/2006 |
| CN | 1857877 | 11/2006 |

(Continued)

OTHER PUBLICATIONS

European Search Report for Application No. 14160093 dated Feb. 3, 2015.

*Primary Examiner* — Lauren P Farrar
*Assistant Examiner* — Hamza A Darb
(74) *Attorney, Agent, or Firm* — Frost Brown Todd LLC

(57) ABSTRACT

A robotic instrument driver for elongate members includes a first carriage positionable on a bed and beside a patient access site for manipulating a first elongate member, and a second carriage positionable proximate the bed, the second carriage configured to articulate the first elongate member, wherein the second carriage is movable independent from the first carriage.

23 Claims, 3 Drawing Sheets

(56) References Cited

U.S. PATENT DOCUMENTS

| | | |
|---|---|---|
| 4,745,908 A | 5/1988 | Wardle |
| 4,748,969 A | 6/1988 | Wardle |
| 4,750,475 A | 6/1988 | Yoshihashi |
| 4,771,766 A | 9/1988 | Aoshiro |
| 4,846,791 A | 7/1989 | Hattler et al. |
| 4,869,238 A | 9/1989 | Opie et al. |
| 4,906,496 A | 3/1990 | Hosono et al. |
| 4,907,168 A | 3/1990 | Boggs |
| 4,967,732 A | 11/1990 | Inoue |
| 5,018,509 A | 5/1991 | Suzuki et al. |
| 5,050,585 A | 9/1991 | Takahashi |
| 5,083,549 A | 1/1992 | Cho et al. |
| 5,106,387 A | 4/1992 | Kittrell et al. |
| 5,108,800 A | 4/1992 | Koo |
| 5,125,909 A | 6/1992 | Heimberger |
| 5,168,864 A | 12/1992 | Shockey |
| 5,217,002 A | 6/1993 | Katsurada |
| 5,251,611 A | 10/1993 | Zehel et al. |
| 5,257,617 A | 11/1993 | Takahashi |
| 5,261,391 A | 11/1993 | Inoue |
| 5,287,861 A | 2/1994 | Wilk |
| 5,313,934 A | 5/1994 | Wiita et al. |
| 5,346,498 A | 9/1994 | Greelis et al. |
| 5,386,818 A | 2/1995 | Schneebaum |
| 5,398,691 A | 3/1995 | Martin et al. |
| 5,408,409 A | 4/1995 | Glassman et al. |
| 5,448,988 A | 9/1995 | Watanabe |
| 5,478,330 A | 12/1995 | Imran et al. |
| 5,482,029 A | 1/1996 | Sekiguchi |
| 5,489,270 A | 2/1996 | van Erp |
| 5,507,725 A | 4/1996 | Savage et al. |
| 5,524,180 A | 6/1996 | Wang et al. |
| 5,533,985 A | 7/1996 | Wang |
| 5,580,200 A | 12/1996 | Fullerton |
| 5,631,973 A | 5/1997 | Green |
| 5,681,296 A | 10/1997 | Ishida |
| 5,704,534 A | 1/1998 | Huitema et al. |
| 5,713,946 A | 2/1998 | Ben-Haim |
| 5,720,775 A | 2/1998 | Larnard |
| 5,741,429 A | 4/1998 | Donadio, III |
| 5,749,362 A | 5/1998 | Funda et al. |
| 5,749,889 A | 5/1998 | Bacich et al. |
| 5,779,623 A | 7/1998 | Bonnell |
| 5,859,934 A | 1/1999 | Green |
| 5,873,817 A | 2/1999 | Kokish et al. |
| 5,876,325 A | 3/1999 | Mizuno et al. |
| 5,879,287 A | 3/1999 | Yoshihashi |
| 5,882,347 A | 3/1999 | Mouris-Laan |
| 5,888,191 A | 3/1999 | Akiba |
| 5,910,129 A | 6/1999 | Koblish et al. |
| 5,938,586 A | 8/1999 | Wilk |
| 5,938,587 A | 8/1999 | Taylor et al. |
| 5,951,475 A | 9/1999 | Gueziec et al. |
| 6,012,494 A | 1/2000 | Balazs |
| 6,143,013 A | 11/2000 | Samson et al. |
| 6,157,853 A | 12/2000 | Blume et al. |
| 6,174,280 B1 | 1/2001 | Oneda |
| 6,197,015 B1 | 3/2001 | Wilson |
| 6,198,974 B1 | 3/2001 | Webster, Jr. |
| 6,226,543 B1 | 5/2001 | Gilboa et al. |
| 6,234,958 B1 | 5/2001 | Snoke et al. |
| 6,259,806 B1 | 7/2001 | Green |
| 6,272,371 B1 | 8/2001 | Shlomo |
| 6,315,715 B1 | 11/2001 | Taylor et al. |
| 6,404,497 B1 | 6/2002 | Backman |
| 6,424,885 B1 | 7/2002 | Niemeyer et al. |
| 6,436,107 B1 | 8/2002 | Wang et al. |
| 6,464,632 B1 | 10/2002 | Taylor |
| 6,485,411 B1 | 11/2002 | Konstorum |
| 6,491,626 B1 | 12/2002 | Stone et al. |
| 6,537,205 B1 | 3/2003 | Smith |
| 6,554,793 B1 | 4/2003 | Pauker et al. |
| 6,716,178 B1 | 4/2004 | Kilpatrick et al. |
| 6,726,675 B1 | 4/2004 | Beyar |
| 6,746,422 B1 | 6/2004 | Noriega |
| 6,749,560 B1 | 6/2004 | Konstorum |
| 6,790,173 B2 | 9/2004 | Saadat |
| 6,827,710 B1 | 12/2004 | Mooney et al. |
| 6,827,712 B2 | 12/2004 | Tovey et al. |
| 6,837,846 B2 | 1/2005 | Jaffe |
| 6,908,428 B2 | 6/2005 | Aizenfeld |
| 6,921,362 B2 | 7/2005 | Ouchi |
| 6,958,035 B2 | 10/2005 | Friedman et al. |
| 7,008,401 B2 | 3/2006 | Thompson et al. |
| 7,130,700 B2 | 10/2006 | Gardeski et al. |
| 7,155,315 B2 | 12/2006 | Niemeyer et al. |
| 7,594,903 B2 | 9/2009 | Webler et al. |
| 7,645,230 B2 | 1/2010 | Mikkaichi et al. |
| 7,645,231 B2 | 1/2010 | Akiba |
| 7,789,827 B2 | 9/2010 | Landry |
| 7,789,874 B2 | 9/2010 | Yu et al. |
| 7,930,065 B2 | 4/2011 | Larkin et al. |
| 8,046,049 B2 | 10/2011 | Govari et al. |
| 8,052,636 B2 | 11/2011 | Moll et al. |
| 8,146,874 B2 | 4/2012 | Yu |
| 8,246,536 B2 | 8/2012 | Ochi |
| 8,444,637 B2 | 5/2013 | Podmore et al. |
| 8,460,236 B2 | 6/2013 | Roelle et al. |
| 8,498,691 B2 | 7/2013 | Moll et al. |
| 8,515,215 B2 | 8/2013 | Younge et al. |
| 8,652,030 B2 | 2/2014 | Matsuura et al. |
| 8,686,747 B2 | 4/2014 | Berner |
| 8,758,231 B2 | 6/2014 | Bunch et al. |
| 8,827,947 B2 | 9/2014 | Bosman et al. |
| 8,968,333 B2 | 3/2015 | Yu et al. |
| 9,023,068 B2 | 5/2015 | Viola |
| 9,186,046 B2 | 11/2015 | Ramamurthy et al. |
| 9,314,306 B2 | 4/2016 | Yu |
| 9,314,953 B2 | 4/2016 | Lauer |
| 9,326,822 B2 | 5/2016 | Lewis et al. |
| 9,408,669 B2 | 8/2016 | Kokish et al. |
| 9,427,551 B2 | 8/2016 | Leeflang et al. |
| 9,452,018 B2 | 9/2016 | Yu |
| 9,504,604 B2 | 11/2016 | Alvarez |
| 9,561,083 B2 | 2/2017 | Yu et al. |
| 9,566,201 B2 | 2/2017 | Yu |
| 9,591,990 B2 | 3/2017 | Chen et al. |
| 9,622,827 B2 | 4/2017 | Yu et al. |
| 9,636,184 B2 | 5/2017 | Lee et al. |
| 9,713,509 B2 | 7/2017 | Schuh et al. |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,844,353 B2 | 12/2017 | Walker et al. |
| 9,844,412 B2 | 12/2017 | Bogusky et al. |
| 9,867,635 B2 | 1/2018 | Alvarez et al. |
| 9,918,659 B2 | 3/2018 | Chopra |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 10,016,900 B1 | 7/2018 | Meyer et al. |
| 10,022,192 B1 | 7/2018 | Ummalaneni |
| 10,080,576 B2 | 9/2018 | Romo et al. |
| 10,130,427 B2 | 11/2018 | Tanner et al. |
| 10,136,959 B2 | 11/2018 | Mintz et al. |
| 10,145,747 B1 | 12/2018 | Lin et al. |
| 10,149,720 B2 | 12/2018 | Romo |
| 10,159,532 B1 | 12/2018 | Ummalaneni et al. |
| 10,159,533 B2 | 12/2018 | Moll et al. |
| 10,169,875 B2 | 1/2019 | Mintz et al. |
| 10,219,874 B2 | 3/2019 | Yu et al. |
| 10,231,793 B2 | 3/2019 | Romo |
| 10,231,867 B2 | 3/2019 | Alvarez et al. |
| 10,244,926 B2 | 4/2019 | Noonan et al. |
| 10,285,574 B2 | 5/2019 | Landey et al. |
| 10,299,870 B2 | 5/2019 | Connolly et al. |
| 10,314,463 B2 | 6/2019 | Agrawal et al. |

(56) References Cited

U.S. PATENT DOCUMENTS

| | | |
|---|---|---|
| 10,376,672 B2 * | 8/2019 | Yu .................... A61B 34/30 |
| 10,426,559 B2 | 10/2019 | Graetzel et al. |
| 10,434,660 B2 | 10/2019 | Meyer |
| 10,464,209 B2 | 11/2019 | Ho et al. |
| 10,470,830 B2 | 11/2019 | Hill |
| 10,482,599 B2 | 11/2019 | Mintz et al. |
| 10,517,692 B2 | 12/2019 | Eyre et al. |
| 10,524,866 B2 | 1/2020 | Srinivasan |
| 10,539,478 B2 | 1/2020 | Lin |
| 10,555,778 B2 | 2/2020 | Ummalaneni et al. |
| 10,639,114 B2 | 5/2020 | Schuh |
| 10,667,875 B2 | 6/2020 | DeFonzo |
| 10,702,348 B2 | 7/2020 | Moll et al. |
| 10,743,751 B2 | 8/2020 | Landey et al. |
| 10,751,140 B2 | 8/2020 | Wallace et al. |
| 10,765,303 B2 | 9/2020 | Graetzel et al. |
| 10,765,487 B2 | 9/2020 | Ho |
| 2001/0004676 A1 | 6/2001 | Ouchi |
| 2003/0036748 A1 | 2/2003 | Cooper et al. |
| 2003/0130564 A1 | 7/2003 | Martone et al. |
| 2003/0158545 A1 | 8/2003 | Hovda et al. |
| 2003/0163199 A1 | 8/2003 | Chu et al. |
| 2003/0195664 A1 | 10/2003 | Nowlin et al. |
| 2004/0015122 A1 | 1/2004 | Zhang et al. |
| 2004/0054322 A1 | 3/2004 | Vargas |
| 2004/0072066 A1 | 4/2004 | Cho et al. |
| 2004/0138525 A1 | 7/2004 | Saadat et al. |
| 2004/0167559 A1 | 8/2004 | Taylor et al. |
| 2004/0193013 A1 | 9/2004 | Isakawa et al. |
| 2004/0249246 A1 | 12/2004 | Campos |
| 2005/0004515 A1 | 1/2005 | Hart et al. |
| 2005/0125005 A1 | 6/2005 | Fujikura |
| 2005/0131279 A1 | 6/2005 | Boulais et al. |
| 2005/0154262 A1 | 7/2005 | Banik et al. |
| 2005/0159646 A1 | 7/2005 | Nordstrom et al. |
| 2005/0165366 A1 | 7/2005 | Brustad |
| 2005/0222581 A1 | 10/2005 | Fischer et al. |
| 2005/0234293 A1 | 10/2005 | Yamamoto |
| 2005/0256452 A1 | 11/2005 | DeMarchi |
| 2005/0272975 A1 | 12/2005 | McWeeney et al. |
| 2005/0273085 A1 | 12/2005 | Hinman et al. |
| 2005/0288549 A1 | 12/2005 | Mathis |
| 2006/0025676 A1 | 2/2006 | Viswanathan et al. |
| 2006/0041188 A1 | 2/2006 | Dirusso et al. |
| 2006/0111692 A1 | 5/2006 | Hlavka et al. |
| 2006/0241368 A1 | 10/2006 | Fichtinger et al. |
| 2006/0264708 A1 | 11/2006 | Horne |
| 2006/0276827 A1 | 12/2006 | Mitelberg et al. |
| 2007/0060879 A1 | 3/2007 | Weitzner et al. |
| 2007/0112355 A1 | 5/2007 | Salahieh |
| 2007/0135733 A1 | 6/2007 | Soukup et al. |
| 2007/0135763 A1 | 6/2007 | Musbach et al. |
| 2007/0135803 A1 | 6/2007 | Belson |
| 2007/0156019 A1 | 7/2007 | Larkin et al. |
| 2007/0270645 A1 | 11/2007 | Ikeda |
| 2007/0270679 A1 | 11/2007 | Nguyen et al. |
| 2007/0282167 A1 | 12/2007 | Barenboym et al. |
| 2007/0287886 A1 | 12/2007 | Saadat |
| 2008/0039255 A1 | 2/2008 | Jinno et al. |
| 2008/0051629 A1 | 2/2008 | Sugiyama et al. |
| 2008/0065103 A1 | 3/2008 | Cooper et al. |
| 2008/0097293 A1 | 4/2008 | Chin et al. |
| 2008/0108869 A1 | 5/2008 | Sanders et al. |
| 2008/0139887 A1 | 6/2008 | Fitpatrick |
| 2008/0146874 A1 | 6/2008 | Miller |
| 2008/0147089 A1 | 6/2008 | Loh |
| 2008/0177285 A1 | 7/2008 | Brock et al. |
| 2008/0208001 A1 | 8/2008 | Hadani |
| 2008/0212082 A1 | 9/2008 | Froggatt et al. |
| 2008/0218770 A1 | 9/2008 | Moll et al. |
| 2008/0245946 A1 | 10/2008 | Yu |
| 2009/0099420 A1 | 4/2009 | Woodley et al. |
| 2009/0163851 A1 | 6/2009 | Holloway |
| 2009/0247880 A1 | 10/2009 | Naruse et al. |
| 2009/0254083 A1 | 10/2009 | Wallace et al. |
| 2009/0262109 A1 | 10/2009 | Markowitz et al. |
| 2009/0299344 A1 | 12/2009 | Lee et al. |
| 2009/0306587 A1 | 12/2009 | Milijasevic et al. |
| 2010/0030023 A1 | 2/2010 | Yoshie |
| 2010/0073150 A1 | 3/2010 | Olson et al. |
| 2010/0114115 A1 | 5/2010 | Schlesinger et al. |
| 2010/0130823 A1 | 5/2010 | Ando |
| 2010/0168918 A1 | 7/2010 | Zhao |
| 2010/0217184 A1 | 8/2010 | Koblish et al. |
| 2010/0249497 A1 | 9/2010 | Peine et al. |
| 2010/0249506 A1 | 9/2010 | Prisco et al. |
| 2011/0009863 A1 | 1/2011 | Stanislaw |
| 2011/0046441 A1 | 2/2011 | Wiltshire et al. |
| 2011/0077681 A1 * | 3/2011 | Nagano ............ A61B 17/12022 606/200 |
| 2011/0098533 A1 | 4/2011 | Onoda |
| 2011/0130718 A1 | 6/2011 | Kidd et al. |
| 2011/0148442 A1 | 6/2011 | Berner |
| 2011/0152880 A1 | 6/2011 | Alvarez et al. |
| 2011/0178508 A1 | 7/2011 | Ullrich |
| 2011/0245844 A1 | 10/2011 | Jinno et al. |
| 2011/0261183 A1 | 10/2011 | Ma et al. |
| 2011/0306836 A1 | 12/2011 | Ohline et al. |
| 2012/0071752 A1 | 3/2012 | Sewell |
| 2012/0071894 A1 * | 3/2012 | Tanner .................. A61B 34/35 606/130 |
| 2012/0071895 A1 | 3/2012 | Stahler et al. |
| 2012/0123327 A1 | 5/2012 | Miller |
| 2012/0136419 A1 | 5/2012 | Zarembo et al. |
| 2012/0143226 A1 | 6/2012 | Belson et al. |
| 2012/0190976 A1 | 7/2012 | Kleinstreuer |
| 2012/0191107 A1 | 7/2012 | Tanner et al. |
| 2012/0239012 A1 | 9/2012 | Laurent et al. |
| 2012/0241576 A1 | 9/2012 | Yu |
| 2012/0259244 A1 | 10/2012 | Roberts et al. |
| 2012/0283747 A1 | 11/2012 | Popovic |
| 2012/0289777 A1 | 11/2012 | Chopra |
| 2013/0018400 A1 | 1/2013 | Milton et al. |
| 2013/0030519 A1 | 1/2013 | Tran et al. |
| 2013/0035537 A1 | 2/2013 | Wallace et al. |
| 2013/0090552 A1 | 4/2013 | Ramamurthy et al. |
| 2013/0109957 A1 | 5/2013 | Hooft et al. |
| 2013/0144116 A1 | 6/2013 | Cooper et al. |
| 2013/0165854 A1 | 6/2013 | Sandhu et al. |
| 2013/0165908 A1 | 6/2013 | Purdy et al. |
| 2013/0172906 A1 * | 7/2013 | Olson .................... A61B 34/74 606/130 |
| 2013/0204124 A1 | 8/2013 | Duindam |
| 2013/0226151 A1 | 8/2013 | Suehara |
| 2013/0303892 A1 | 11/2013 | Zhao |
| 2013/0304091 A1 | 11/2013 | Straehnz |
| 2013/0317276 A1 | 11/2013 | D'Andrea |
| 2013/0317519 A1 | 11/2013 | Romo et al. |
| 2013/0345519 A1 | 12/2013 | Piskun et al. |
| 2014/0012288 A1 | 1/2014 | Darisse |
| 2014/0046313 A1 | 2/2014 | Pederson et al. |
| 2014/0142591 A1 | 5/2014 | Alvarez et al. |
| 2014/0200402 A1 | 7/2014 | Snoke et al. |
| 2014/0235943 A1 | 8/2014 | Paris |
| 2014/0276391 A1 | 9/2014 | Yu |
| 2014/0276594 A1 | 9/2014 | Tanner et al. |
| 2014/0276647 A1 | 9/2014 | Yu |
| 2014/0276935 A1 | 9/2014 | Yu |
| 2014/0276936 A1 | 9/2014 | Kokish et al. |
| 2014/0277333 A1 | 9/2014 | Lewis et al. |
| 2014/0277334 A1 | 9/2014 | Yu et al. |
| 2014/0316397 A1 | 10/2014 | Brown |
| 2014/0343416 A1 | 11/2014 | Panescu |
| 2014/0357984 A1 | 12/2014 | Wallace et al. |
| 2014/0364870 A1 | 12/2014 | Alvarez et al. |
| 2015/0031950 A1 | 1/2015 | Drontle et al. |
| 2015/0051592 A1 | 2/2015 | Kintz |
| 2015/0133858 A1 | 5/2015 | Julian et al. |
| 2015/0164594 A1 | 6/2015 | Romo et al. |
| 2015/0164596 A1 | 6/2015 | Romo |
| 2015/0255782 A1 | 9/2015 | Kim et al. |
| 2015/0327939 A1 | 11/2015 | Kokish et al. |
| 2015/0335480 A1 | 11/2015 | Alvarez et al. |
| 2016/0000414 A1 | 1/2016 | Brown |

(56) References Cited

U.S. PATENT DOCUMENTS

| | | |
|---|---|---|
| 2016/0001038 A1 | 1/2016 | Romo et al. |
| 2016/0007881 A1 | 1/2016 | Wong et al. |
| 2016/0067450 A1 | 3/2016 | Kowshik |
| 2016/0100896 A1 | 4/2016 | Yu |
| 2016/0151122 A1 | 6/2016 | Alvarez et al. |
| 2016/0183841 A1 | 6/2016 | Duindam et al. |
| 2016/0227982 A1 | 8/2016 | Takahashi |
| 2016/0235946 A1 | 8/2016 | Lewis et al. |
| 2016/0270865 A1 | 9/2016 | Landey et al. |
| 2016/0287279 A1 | 10/2016 | Bovay et al. |
| 2016/0287346 A1 | 10/2016 | Hyodo et al. |
| 2016/0338785 A1 | 11/2016 | Kokish et al. |
| 2016/0346049 A1 | 12/2016 | Allen et al. |
| 2016/0354582 A1 | 12/2016 | Yu et al. |
| 2016/0372743 A1 | 12/2016 | Cho et al. |
| 2016/0374590 A1 | 12/2016 | Wong et al. |
| 2017/0007337 A1 | 1/2017 | Dan |
| 2017/0007343 A1 | 1/2017 | Yu |
| 2017/0100199 A1 | 4/2017 | Yu et al. |
| 2017/0105804 A1 | 4/2017 | Yu |
| 2017/0119481 A1 | 5/2017 | Romo et al. |
| 2017/0165011 A1 | 6/2017 | Bovay et al. |
| 2017/0172673 A1 | 6/2017 | Yu et al. |
| 2017/0202627 A1 | 7/2017 | Sramek et al. |
| 2017/0209073 A1 | 7/2017 | Sramek et al. |
| 2017/0281218 A1 | 10/2017 | Timm |
| 2017/0290631 A1 | 10/2017 | Lee et al. |
| 2017/0333679 A1 | 11/2017 | Jiang |
| 2017/0340396 A1 | 11/2017 | Romo et al. |
| 2017/0367782 A1 | 12/2017 | Schuh et al. |
| 2018/0025666 A1 | 1/2018 | Ho et al. |
| 2018/0055589 A1 | 3/2018 | Joseph et al. |
| 2018/0177556 A1 | 6/2018 | Noonan et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289431 A1 | 10/2018 | Draper et al. |
| 2018/0325499 A1 | 11/2018 | Landey et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000576 A1 | 1/2019 | Mintz et al. |
| 2019/0105110 A1 | 4/2019 | Tanner et al. |
| 2019/0110839 A1 | 4/2019 | Rafii-Tari et al. |
| 2019/0151148 A1 | 4/2019 | Alvarez et al. |
| 2019/0167366 A1 | 6/2019 | Ummalaneni |
| 2019/0175009 A1 | 6/2019 | Mintz |
| 2019/0175062 A1 | 6/2019 | Rafii-Tar et al. |
| 2019/0175799 A1 | 6/2019 | Hsu |
| 2019/0183585 A1 | 6/2019 | Rafii-Tar et al. |
| 2019/0183587 A1 | 6/2019 | Rafii-Tari et al. |
| 2019/0216548 A1 | 7/2019 | Ummalaneni |
| 2019/0216576 A1 | 7/2019 | Eyre |
| 2019/0223974 A1 | 7/2019 | Romo |
| 2019/0228525 A1 | 7/2019 | Mintz et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298460 A1 | 10/2019 | Al-Jadda |
| 2019/0298465 A1 | 10/2019 | Chin |
| 2019/0336238 A1 | 11/2019 | Yu |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0375383 A1 | 12/2019 | Alvarez |
| 2019/0380787 A1 | 12/2019 | Ye |
| 2019/0380797 A1 | 12/2019 | Yu |
| 2020/0000533 A1 | 1/2020 | Schuh |
| 2020/0022767 A1 | 1/2020 | Hill |
| 2020/0038128 A1 | 2/2020 | Joseph |
| 2020/0039086 A1 | 2/2020 | Meyer |
| 2020/0046434 A1 | 2/2020 | Graetzel |
| 2020/0046942 A1 | 2/2020 | Alvarez |
| 2020/0054408 A1 | 2/2020 | Schuh et al. |
| 2020/0060516 A1 | 2/2020 | Baez |
| 2020/0093549 A1 | 3/2020 | Chin |
| 2020/0093554 A1 | 3/2020 | Schuh |
| 2020/0100845 A1 | 4/2020 | Julian |
| 2020/0100855 A1 | 4/2020 | Leparmentier |
| 2020/0101264 A1 | 4/2020 | Jiang |
| 2020/0107894 A1 | 4/2020 | Wallace |
| 2020/0121502 A1 | 4/2020 | Kintz |
| 2020/0146769 A1 | 5/2020 | Eyre |
| 2020/0188043 A1 | 6/2020 | Yu |
| 2020/0197112 A1 | 6/2020 | Chin |
| 2020/0206472 A1 | 7/2020 | Ma |
| 2020/0217733 A1 | 7/2020 | Lin |
| 2020/0222134 A1 | 7/2020 | Schuh |
| 2020/0237458 A1 | 7/2020 | DeFonzo |
| 2020/0261172 A1 | 8/2020 | Romo |
| 2020/0268459 A1 | 8/2020 | Noonan et al. |
| 2020/0268460 A1 | 8/2020 | Tse |

FOREIGN PATENT DOCUMENTS

| | | |
|---|---|---|
| CN | 102316817 | 1/2012 |
| CN | 102458295 | 5/2012 |
| CN | 102665590 | 9/2012 |
| CN | 102711586 | 10/2012 |
| CN | 102973317 | 3/2013 |
| CN | 103767659 | 5/2014 |
| CN | 103930063 | 7/2014 |
| EP | 0 543 539 | 5/1993 |
| EP | 0 776 739 | 6/1997 |
| EP | 1 442 720 | 8/2004 |
| EP | 0 904 796 | 11/2004 |
| JP | 2006-525087 | 11/2006 |
| JP | 2007-511247 | 5/2007 |
| JP | 2010-046364 | 3/2010 |
| JP | 2011-015992 | 1/2011 |
| JP | 2012-105793 | 6/2012 |
| WO | WO 94/14494 | 7/1994 |
| WO | WO 00/67640 | 11/2000 |
| WO | WO 02/74178 | 9/2002 |
| WO | WO 03/086190 | 10/2003 |
| WO | WO 04/039273 | 5/2004 |
| WO | WO 04/105849 | 12/2004 |
| WO | WO 05/032637 | 4/2005 |
| WO | WO 05/081202 | 9/2005 |
| WO | WO 07/14687 | 12/2007 |
| WO | WO 08/097540 | 8/2008 |
| WO | WO 09/092059 | 7/2009 |
| WO | WO 09/097461 | 8/2009 |
| WO | WO 10/081187 | 7/2010 |
| WO | WO 11/005335 | 1/2011 |
| WO | WO 11/058493 | 5/2011 |
| WO | WO 13/107468 | 7/2013 |
| WO | WO 16/003052 | 1/2016 |
| WO | WO 15/093602 | 3/2017 |

\* cited by examiner

CATHETER INSERTION SYSTEM AND METHOD OF FABRICATION

CROSS-REFERENCE TO RELATED APPLICATION

This application is a continuation of U.S. patent application Ser. No. 13/832,352, filed on Mar. 15, 2013, entitled "CATHETER INSERTION SYSTEM AND METHOD OF FABRICATION," issued as U.S. Pat. No. 10,376,672 on Aug. 13, 2019. The foregoing application is hereby incorporated by reference herein in its entirety.

BACKGROUND

Robotic interventional systems and devices are well suited for performing minimally invasive medical procedures as opposed to conventional techniques wherein a patient's body cavity is open to permit a surgeon's hands to have access to internal organs. Advances in technology have led to significant changes in the field of medical surgery such that less invasive surgical procedures, in particular, minimally invasive surgery (MIS), are increasingly popular.

MIS is generally defined as surgery performed by entering the body through the skin, a body cavity, or an anatomical opening utilizing small incisions rather than large, open incisions in the body. With MIS, it is possible to achieve less operative trauma for the patient, reduced hospitalization time, less pain and scarring, reduced incidence of complications related to surgical trauma, lower costs, and a speedier recovery.

MIS apparatus and techniques have advanced to the point where an elongated catheter instrument is controllable by selectively operating tensioning control elements within the catheter instrument. At least two types of catheters may be employed for surgical procedures. One type includes an electrophysiology (EP) catheter typically uses a navigating distance of 15 cm or less. EP catheters also may be relatively thick and stiff and thus, due their short length and high stiffness, EP catheters typically do not suffer from a tendency to buckle during use.

In comparison to EP procedures, vascular procedures include a greater amount of catheter insertion length, a greater number of catheter articulation degrees of freedom (DOFs), and a mechanism for manipulation of a guide wire. For that reason, a bedside system provides mounting for splayer actuation hardware configured to provide the catheter insertion lengths, mounting which accounts for an increase in splayer size due to added DOFs, and mounting for a guide wire manipulator. Thus, vascular catheters typically include a relatively long stroke, such as one meter or more. Relative to EP catheters, vascular catheters are typically smaller, thinner, and more flexible, and therefore have a greater tendency to buckle than EP catheters. As such, it is typically desirable to feed vascular catheters into the patient with minimal bending to reduce the tendency to buckle. Known vascular robotic catheter systems are therefore typically suspended over the patient that is lying prone on a bed.

A vascular catheter system typically includes elongate members that include an outer catheter (sheath), an inner catheter (leader), and a guidewire. Each is separately controllable and therefore they can telescope with respect to one another. For instance, a sheath carriage controls operation of the sheath and is moveable in a generally axial motion along the patient, and a leader carriage controls operation of the guidewire and is likewise moveable in the generally axial direction of the patient. Typically, the leader carriage and the sheath carriage are positioned on a remote catheter manipulator (RCM), which is supported by a setup joint (SUJ). The SUJ is typically positioned on a rail that is itself mounted to the bed, below which the patient is positioned.

As such, the RCM typically carries the weight of both carriages as well as the other hardware that are used to operate the system. And, to provide the full stroke, the SUJ is passed through the full range of motion which, as stated, can exceed one meter. To do so, typically the SUJ is moved or rotated with respect to the rail and the rail is stationary. For this reason, a bedside system is typically included that provides mounting for splayer actuation hardware configured to provide catheter insertion lengths, and mounting for a guide wire manipulator. Because this hardware is mounted on the rail, the system can not only be cumbersome to work with, but it can interfere with other system operation (such as the C-arm and monitors), as well as provide significant weight that is carried by the bed.

Thus, there is a need to for an improved catheter system that operates over a smaller footprint, weighs less, and does not compromise the propensity for the catheter to buckle.

SUMMARY

A robotic instrument driver for elongate members includes a first carriage positionable on a bed and beside a patient access site for manipulating a first elongate member, and a second carriage positionable proximate the bed, the second carriage configured to articulate the first elongate member, wherein the second carriage is movable independent from the first carriage.

A catheter surgical system coupled to a bed configured to support a patient during surgery, the system includes a first carriage configured to couple to the bed and to manipulate a first elongate member, and a second carriage configured to couple to the bed adjacent to where the patient is positioned during surgery, wherein the second carriage is configured to articulate the first elongate member, and the second carriage is moveable autonomously from the first carriage.

A method of assembling a catheter insertion system includes providing a first carriage that is positionable proximate a patient surgical support structure, the first carriage configured to manipulate an elongate member into a patient, and providing a second carriage that is positionable proximate the patient surgical support structure and beside a patient on the patient surgical support structure, wherein the second carriage is configured to articulate the first elongate member and is moveable independently from the first carriage.

BRIEF DESCRIPTION OF THE DRAWINGS

While the claims are not limited to a specific illustration, an appreciation of the various aspects is best gained through a discussion of various examples thereof. Referring now to the drawings, exemplary illustrations are shown in detail. Although the drawings represent the illustrations, the drawings are not necessarily to scale and certain features may be exaggerated to better illustrate and explain an innovative aspect of an example. Further, the exemplary illustrations described herein are not intended to be exhaustive or otherwise limiting or restricted to the precise form and configuration shown in the drawings and disclosed in the following detailed description. Exemplary illustrations are described in detail by referring to the drawings as follows:

DETAILED DESCRIPTION

Figure 1:
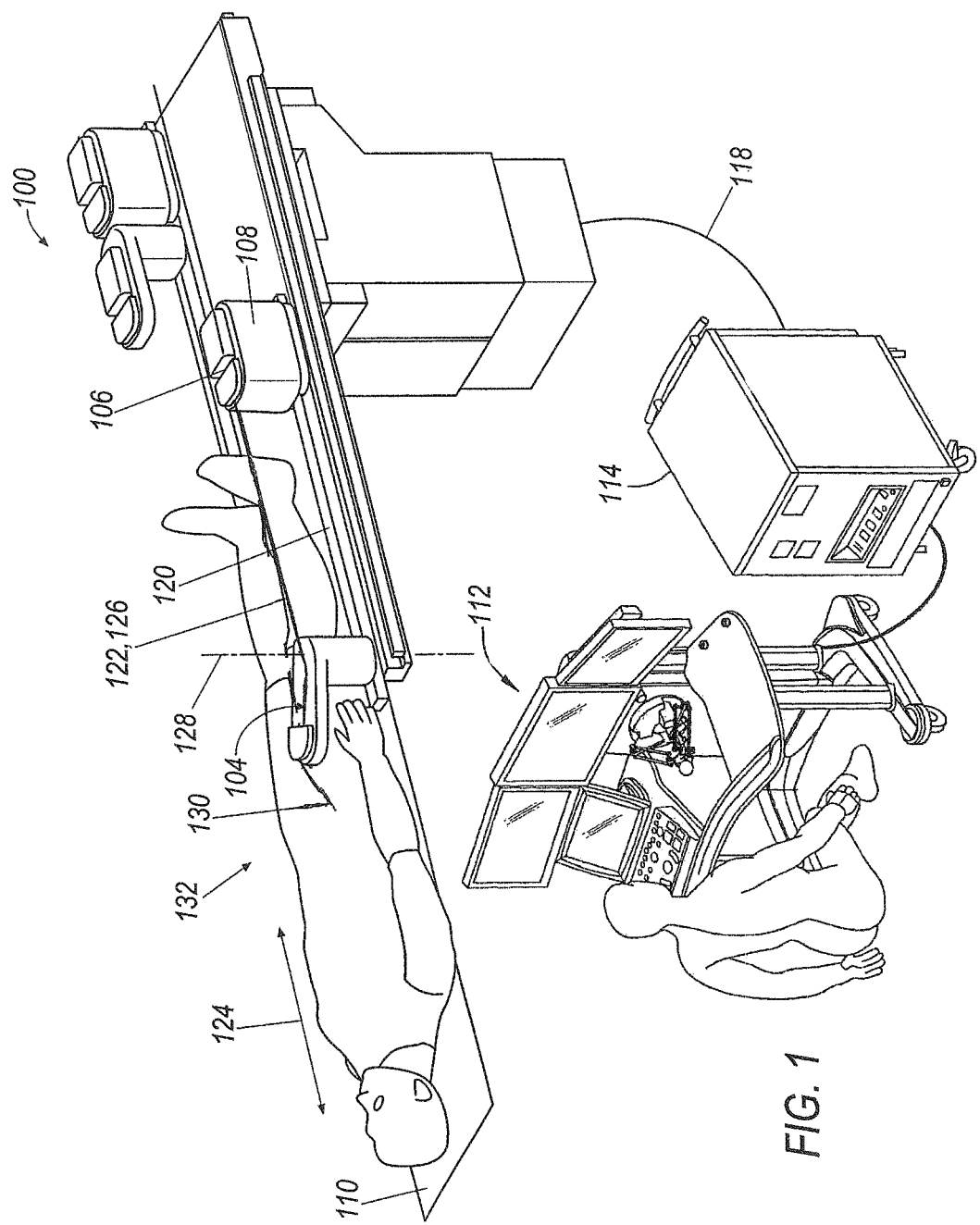
FIG. 1 is a perspective view of an illustration of a robotically controlled surgical system, according to one exemplary illustration.
Figure 2:
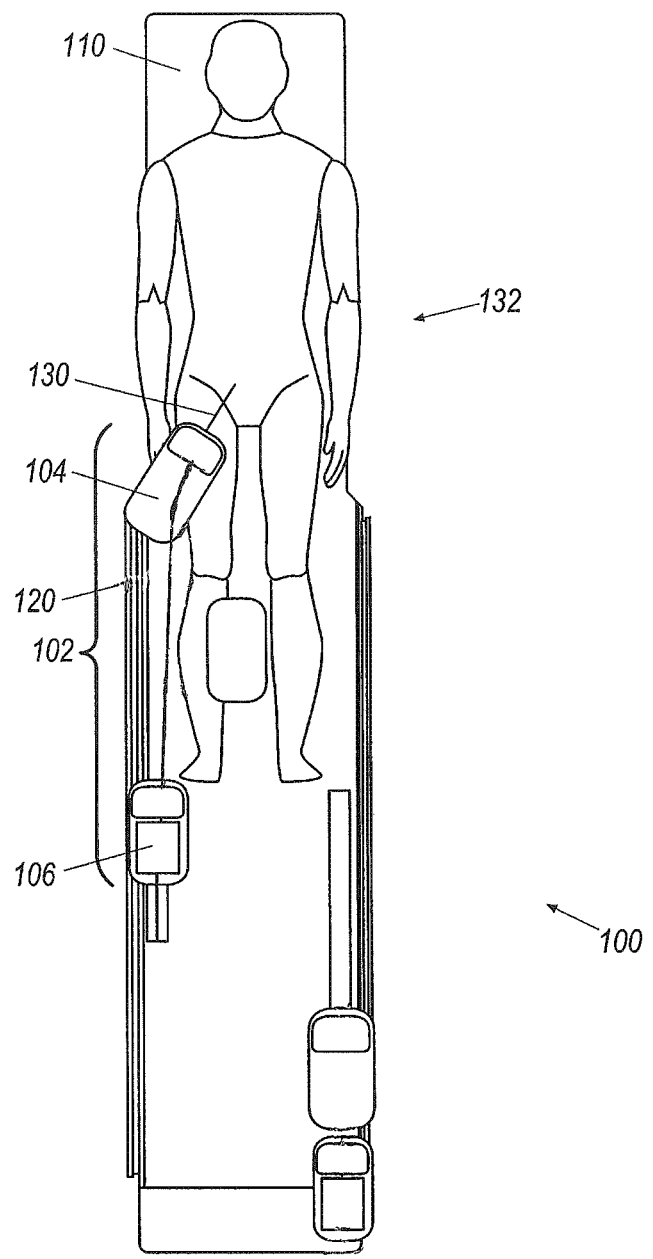
FIG. 2 illustrates a plan view of the system of FIG. 1.

Referring to FIGS. 1 and 2, a robotically controlled surgical system 100 is illustrated in which an apparatus, a system, and/or method may be implemented according to various exemplary illustrations. System 100 includes a robotic instrument driver or catheter insertion system 102 having a robotic or first or outer steerable complement, otherwise referred to as a sheath instrument or sheath carriage 104 and an inner steerable component or otherwise referred to as a leader carriage 106 on a base 108.

During use, a patient is positioned on an operating table or surgical bed 110 (generally referred to as "operating table") to which sheath carriage 104 and leader carriage 106 are coupled or mounted. In the illustrated example, system 100 includes an operator workstation 112, an electronics rack 114 and an associated bedside electronics box (not shown). Surgical bed 110 is positioned on a base or support 116. A surgeon is seated at operator workstation 112 and can monitor the surgical procedure, patient vitals, and control one or more catheter devices.

System components may be coupled together via a plurality of cables or other suitable connectors 118 to provide for data communication, or one or more components may be equipped with wireless communication components to reduce or eliminate cables 118. Communication between components may also be implemented over a network or over the internet. In this manner, a surgeon or other operator may control a surgical instrument while being located away from or remotely from radiation sources, thereby decreasing radiation exposure. Because of the option for wireless or networked operation, the surgeon may even be located remotely from the patient in a different room or building.

FIG. 2 is a plan view of system 100 of FIG. 1 (with workstation 112 and electronics rack 114 omitted). As seen in FIGS. 1 and 2, robotic instrument driver 102 includes a rail 120 on which sheath carriage 104 and leader carriage 106 are positioned and to which they are coupled. Both carriages 104, 106 are positioned proximate bed 110 and in one embodiment are positioned on rail 120, which itself is positioned on and attached to bed 110. Rail 120, in the illustrated embodiment, is positioned beside the patient. That is, rail 120 is positioned proximate a location on the bed where the patient lies during a surgical procedure.

An elongate member 122 that may include an inner catheter and/or guidewire extends between sheath carriage 104 and leader carriage 106, and generally along a length direction 124 for bed 110. Carriages 104, 106 are also each moveable along rail 120 and along direction 124, which in one embodiment is defined also as an advancement axis for elongate elements of the catheter. According to one embodiment, direction 124 also corresponds to a longitudinal axis of bed 120, which generally corresponds to a length direction of the patient. However, it is contemplated that carriages 104, 106 may also be positioned with respect to one another and at an angular orientation with respect to the longitudinal axis of the patient positioned on bed 110. That is, in one embodiment (not shown) rail 120 is positioned at an angle (other than zero degrees) with respect to the longitudinal axis of the patient to better angle components of the catheter with respect to the patient. Leader carriage 106 is configured to advance or retract elongate member 122 when leader carriage 106 is moved along a guidewire axis 126 that is defined as an axis between sheath carriage 104 and leader carriage 106. Each carriage 104, 106 is positionable proximate bed 110 and positionable beside a patient on bed 110, and also repositionable during surgery. Carriage 104, 106 are each moveable independently or autonomously from one another.

Sheath carriage 104 is rotatable about a sheath carriage rotation axis 128. Axis 128 is, in the illustrated embodiment, generally and approximately orthogonal to guidewire axis 126, and also generally orthogonal to direction 124. In such fashion, a sheath 130 is extendable (for instance, during surgery) from sheath carriage 104 and is also directable to optimize an approach angle of elongate element(s) 130 with respect to the patient and to an access site 132 which, in the illustrated instance, is proximate a groin of the patient. Thus sheath 130 and other elongate members extending therefrom may be controllably rotated (or angled) with respect to the patient.

Further, it is contemplated that a sterile drape is positionable on system 100. That is, a sterile drape (not shown) may be positioned between the patient and between catheter assembly 102 such that components of catheter assembly 102 (i.e., carriages 104, 106) are isolated from the patient.

Figure 3:
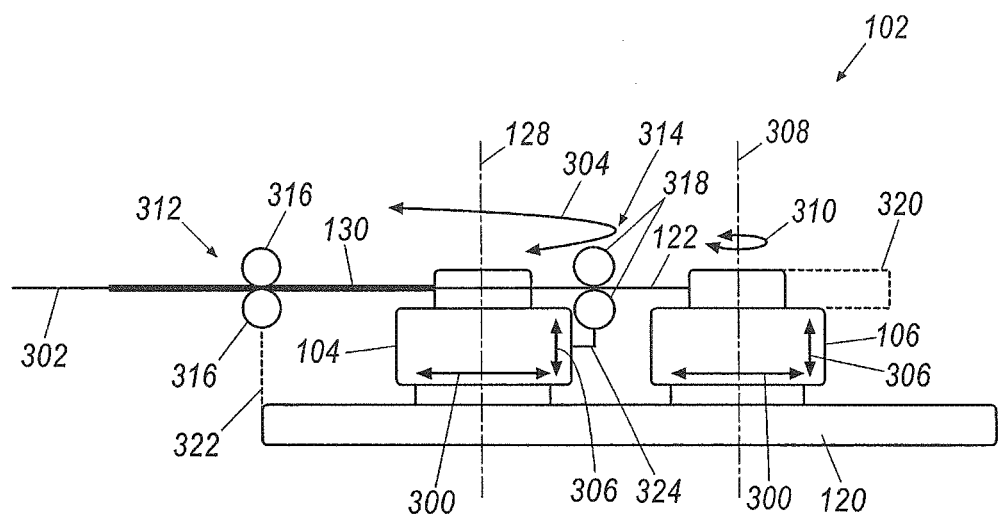
FIGS. 3 and 4 illustrate exemplary components of the catheter insertion of FIGS. 1 and 2.

FIG. 3 illustrates components of the robotic instrument driver of FIGS. 1 and 2. As discussed, robotic instrument driver 102 includes sheath carriage 104 and leader carriage 106 positioned on rail 120. Each carriage 104, 106 is moveable 300 axially with respect to the other, as well as with respect to rail 120. Elongate member 122 extends between carriages 104, 106 and passes through carriage 104 within sheath 130. More generally, catheter or elongate member(s) 302 extend from sheath carriage 104 and catheter 302 may include, as an example, an outer sheath or catheter, an inner catheter, and a guidewire. Sheath carriage 104 is rotatable about axis 128 such that a yaw angle 304 can be imparted to catheter 302. Further, each carriage 104, 106 may have a lift 306 imparted thereto as well, to cause a vertical motion and better position catheter 302 during operation, and to adjust to variation in patient thickness. In addition, leader carriage 106 may also be rotatable about an axis 308 such that a yaw angle 310 may be imparted thereto as well, also to reduce the propensity for catheter 302 to buckle during operation.

The sheath carriage 104 and leader carriage 106 (or pods) may contain an articulation mechanism for steering the pullwires of a catheter (not shown) and a manipulation mechanism for inserting, retracting and rolling an elongate member. The articulation mechanism typically involves 3 or 4 pulleys in the splayer of the catheter attaching to corresponding output shafts in the carriage, the output shaft being driven by motor within the pod. The steering wires running through the wall of the catheter are wrapped around the pulleys as articulation is commanded, resulting in bending of the catheter tip. The manipulation mechanism on the sheath carriage 314 is shown as a pair of feed rollers 318. The manipulation mechanism on the leader carriage is shown as a gripping pad 320. These are exemplary manipulation or active drive mechanisms. It should be understood that any active drive mechanism such as grippers, or chuck mechanism or compressible rollers may be used. In addition, there may be a manipulation mechanism positioned next to the patient access site 132 to constrain and insert, retract, and/or roll sheath 130 into the patient. Active drive mechanism 312 include wheels 316, in one embodiment, that cause sheath 130 to be inserted into a patient, which act in concert with sheath carriage 104 to articulate sheath 130, wherein articulation of the catheter generally refers to steering and selectively positioning the catheter. Similarly, active drive mechanism 314 includes wheels 318, in one embodiment, that cause leader 122 to be inserted into a patient, which act in concert with leader carriage 106 to articulate leader 122, wherein articulation of the catheter generally refers to steering and selectively positioning the catheter. Similarly, active drive mechanism 320, in one embodiment may be attached to carriage 106 to manipulate a guidewire that passes through the center of, and is part of, catheter 302. Active drive mechanism 312 is coupled to rail 120 and will usually not move relative to the patient. Sheath carriage 104, and leader carriage 106 may move relative to 312 and be controlled via workstation 112.

Thus, as shown in FIG. 3, robotic instrument driver 102 includes carriage 104 and its corresponding active drive mechanism 314, carriage 106 and its corresponding active drive mechanism 320 and active drive mechanism 312 that is directly coupled and stationary with respect to rail 120 via a support 322. Support 322 may include a support structure or attachment method to support wheels 316 while allowing wheels 316 to rotate and be driven, to drive sheath 130. Active drive mechanism 314 is attached to carriage 104 via its connection or attachment 324.

It is contemplated that active drive mechanism 312 is positioned proximate the patient and is configured to manipulate (insert, retract or roll) sheath 130 into or out of the patient. Carriage 104 is moveable with respect to rail 120 and, hence, with respect to active drive mechanism 312. Active drive mechanism 314 is therefore also moveable with respect to rail 120 and with respect to carriage 106 as well. Carriages 104 and 106 are therefore moveable independent from one another.

It is contemplated according to one example, that catheter assembly 102 does not include carriage 106. It is also contemplated according to another example, that catheter assembly 102 does not include carriage 106 or drive mechanism 318. That is, assembly 102 may be a robotic instrument driver 102 for driving one or more elongate members that includes a first carriage 312 that is positionable to or on bed 110 for inserting, retracting or roll a sheath 130 into or out of a patient. Robotic instrument driver 102 also includes a second carriage such as carriage 104 that is positionable proximate to or on bed 110 that is configured to articulate sheath 130, wherein the second carriage 104 is movable independent from the first 312. The second carriage 104 is configured for inserting, retracting or rolling a second elongate member such as an inner catheter, which is articulable from a third carriage, such as carriage 106. Further, third carriage 106 is configured in another example to insert, retract or roll a third elongate member that may be, for instance, a guidewire.

Figure 4:
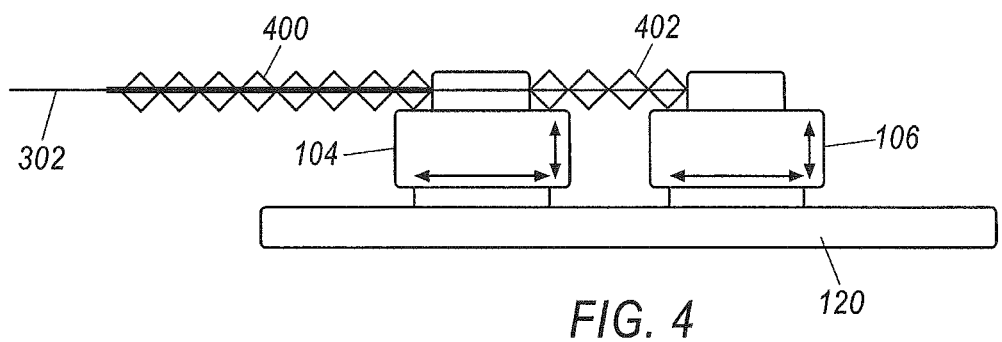

FIG. 4 illustrates an exemplary anti-buckling mechanism that may be incorporated, to reduce the propensity for catheter 302 to buckle during operation, and in lieu of mechanisms 312, 316. Referring to FIG. 4, a scissors-like mechanism may be placed onto catheter 302. The scissors-like mechanism may be a collapsible passive mechanism fabricated from, for instance, plastic or metal, and of such a mass that the catheter extends therethrough with a scissors-action. The mechanism may be positioned between sheath carriage 104 and the patient access site 132 as mechanism 400, and/or between carriages 104, 106 as mechanism 402.

Thus, in general, system 100 includes catheter insertion system 102 having carriages 104, 106. Carriages 104, 106 may otherwise be referred to as lightweight pods that are separately and independently positionable with respect to one another. As such, system 102 avoids using an SUJ and the masses or pods are lightweight, reducing the overall mass of system 100. Carriages 104, 106 are scalable in that they can be sized according to further system catheter needs that may develop over time. Carriages 104, 106 have a low profile and a low height (compared to systems having an SUJ), thus reducing the propensity to interfere with other system equipment. Operation of carriages 104, 106 may also allow for full fluoroscopic image run-off on lower extremity cases, and their operation is not sensitive to different catheter lengths. Further, additional pod/rail combinations could be included within system 100. That is, one or more additional catheter control systems could be placed onto the bed to support further catheter procedures (for instance, a second set of pods on a rail could be included on the bed and on the opposite side of the patient, and perhaps at a different axial location, than that shown in FIGS. 1 and 2). Further, carriages or pods 104, 106 can be easily detachable, supporting a clean and simple method for changing out system components between or during catheterization procedures. The pods and rails shown are aligned to the access site in the femoral artery of the patient. It should be understood that the pods and rails can be set up toward the head of the bed for access sites in the brachial, carotid or auxiliary arteries.

The disclosed bedside system can be very lightweight and provide simpler mechanics for the operating mechanisms. Also, it effectively minimizes wasted catheter length. The disclosed system is a scalable design allowing for the addition of any number of pods for various other manipulators for other tools if desired. Thus, splayers and their actuating motors may be mounted in pods, according to one embodiment. As described, each carrier or pod can have Z axis (up and down) and yaw adjustment, whether manual or robotic. The adjustments can be used to alter the insertion angle of the catheter into the patient. In the disclosed system, the pods may also be mounted to motorized bedside rails providing actuation in the insert/retract directions, as well. There is also no need for setup arms, and interference with C-arm movement is reduced or eliminated. Also, pods could be easily added to the rail making the system very scalable for other system configurations. According to one option, pods are swappable such that one pod that is designed to carry a catheter for example can be swapped with another pod that is designed to carry a tool such as a motorized scalpel, grasper, ablation catheter, etc. In this manner, pods can be swapped mid-procedure depending on which surgical tools are desired during a given procedure.

In some embodiments, the pods contain motors and encoders within the pod to drive operation. A y-axis motor can include a pinion or capstan to interface with the rail via a rack or mechanical cable, respectively. A z-axis motor can connect to a leadscrew, to drive one or multiple stages, to raise and telescope as required. Other z-axis concepts can include a scissor mechanism for extended vertical range. The yaw axis motor can connect to a belt and pulley or gears to rotate the pod. Rotational backlash can be minimized by a miniature harmonic drive gearbox at the motor output. The pod height is determined, in one example, from the table top to the top of the thinnest person's leg, mattress included. The height, in other words, includes the volume below the cantilevered deck.

The rail may include a slide or track, a rack or mechanical cables, and electrical cable harnesses for each pod. The rail can be deployable in one embodiment, meaning it is stowed at the back of the bed and slides into position before use. An alternative is to have a very long rail reach from the end of the bed to the patient's target. The rail can also have a lateral axis to provide patient lateral adjustment and to slide to each side of the table.

The y-axis (up down), z-axis (along the patient), and yaw axis are servo controlled, in one embodiment. In this example, manual set-up is via a pendant or button mounted control. This means that yaw, insertion, and height may be adjusted relative to the target prior to driving. Pods may move in unison vertically. Synchronous pod motion may be used to insert and retract the catheter. The pods may also yaw on a horizontal trajectory while the catheter is inserted and retracted. If inserting and retracting on a fixed pitched angle, say 10°, height may be synchronized as well, resulting in a diving trajectory.

One challenge often experienced with robotically controlled surgical systems is alignment of carriage 104 with the access site of the patient, especially as it approaches the patient. To address misalignment concerns, typically the operator manually maneuvers the carriage 104 (without the sheath 130 attached) into a "fully inserted" position, whereby a nose of the instrument driver 102 is aligned and in close proximity to the access site. The operator would then initiate a "set site" position to effectively teach the carriage 104 the "fully inserted" position. The carriage 104 would then be retracted and the sheath 130 installed. Once installed, the carriage 104 could then be operated to insert the sheath 130 to the installed position. As may be appreciated, the workflow for this procedure is burdensome and time consuming.

To address the above issues, one or more sensors 500 may be attached to the instrument driver 102. This present disclosure contemplates that a variety of sensors 500 may be employed. Such sensors 500 include, but are not limited to a camera, a stereo camera, a range finder, an inclinometer, and a laser beam. These various sensors 500 may be used individually or in combination with one another.

With respect to use of a camera as sensor 500, in one exemplary arrangement, the camera may be mounted on the instrument driver 102 in any suitable location. For embodiments that include a setup joint SUJ, the camera may alternatively be mounted to the SUJ. In one exemplary configuration, the camera is mounted on the nose 502 of the instrument driver 102. The camera would provide a video feed to the workstation 112 to allow the surgeon to visually monitor the access site as the instrument driver 102 approaches the access site. In one exemplary configuration, the video feed could be displayed as a sub-window on the workstation 112 monitor. In this manner, the surgeon would be able to monitor the surgical site, as well as monitor any potential binding of an anti-buckling device, movement or loosing of a stabilizer, and any issues at the access site.

A stereo camera could be coupled with the visual camera. The stereo camera is configured to provide distance information to various points in the image.

Similar to the stereo camera, a range finder may also be employed. The range finder may be used in isolation to measure distance to the access site (for example to prevent collisions with the patient) or in conjunction with a camera image to infer depth of one of several points in the image. The range finder may utilize laser, ultrasonic, or other technology.

The inclinometer would directly measure a pitch angle of the instrument driver 102, thereby allowing adjustments to the instrument driver 102 to align with the access site.

A laser beam may be used to project a simple pointing vector off the nose 502 of the instrument driver 102. Alternatively, the laser may be used to project a reference point onto the camera image. In one exemplary configuration, if the laser and camera are not collocated, then the location of the reference point in the image may be used to infer depth.

In another exemplary configuration, an automated environmental feedback mechanism may be employed in lieu of a sensor. The automated environmental feedback mechanism utilizes a beam of known speed, for example light. To set an insertion site trajectory the beam, for example in the form of a pulsating LED, would be emitted from the front of the instrument driver 102 to a reflective target on a patient patch. An array of areas for providing a return reading would be positioned on the instrument driver 102. Distance from the front of the patient may be determined by calculating the time for a signal return. Angle may also be geometrically determined by the point of return. These data points may be then be used to electronically change the angle of the instrument driver 102 or carriage 104, as well as determine if the instrument driver 102 or carriage 104 should stop a forward or insertion movement. In one exemplary arrangement, the placement of spaced LEDs around the perimeter of the instrument driver 102 would permit use of algorithms by a computer system operatively connected to the workstation 112 and the instrument driver 102 would permit the location of the instrument driver 102 to be determined relative to other pieces of equipment in the surgical suite.

While described in the context of using an LED as the beam, it is understood that any beam having a known speed and refractive qualities (i.e., the ability to reflect from the patient or a suitable patch as opposed to being absorbed or passing through) may be used. Further examples include laser beams and radar.

It will be appreciated that the aforementioned method and devices may be modified to have some components and steps removed, or may have additional components and steps added, all of which are deemed to be within the spirit of the present disclosure. Even though the present disclosure has been described in detail with reference to specific embodiments, it will be appreciated that the various modifications and changes can be made to these embodiments without departing from the scope of the present disclosure as set forth in the claims. The specification and the drawings are to be regarded as an illustrative thought instead of merely restrictive thought.

What is claimed is:

1. A robotic instrument driver, comprising:
   (a) a first pod comprising:
      (i) a first manipulation mechanism configured to articulate one or more steering wires in a first elongate member, and
      (ii) a first active drive mechanism fixed relative to the first manipulation mechanism, the first active drive mechanism configured to insert or retract a second elongate member with respect to the first elongate member,
      wherein the first pod is configured to be movable vertically, wherein the first pod is further configured to be rotatable about a first yaw axis; and
   (b) a second pod comprising:
      (i) a second manipulation mechanism configured to articulate one or more steering wires in the second elongate member, and
      (ii) a second active drive mechanism fixed relative to the second manipulation mechanism and configured to insert or retract a third elongate member with respect to the second elongate member, wherein the second pod is configured to be movable vertically, wherein the second pod is further configured to be rotatable about a second yaw axis.

2. The robotic instrument driver of claim 1, wherein the first active drive mechanism is of a type that is different from the second active drive mechanism.

3. The robotic instrument driver of claim 1, further comprising a third active drive mechanism, wherein the third active drive mechanism is configured to insert or retract the first elongate member.

4. The robotic instrument driver of claim 1, wherein the first yaw axis is approximately orthogonal to an advancement axis along which at least the first pod is moveable.

5. The robotic instrument driver of claim 1, wherein the first pod and the second pod are both positioned on a rail, and the rail is attached to a bed.

6. The robotic instrument driver of claim 1 further comprising an anti-buckling device placed on or around the first elongate member.

7. The robotic instrument driver of claim 1, wherein the first and second pods are configured to be rotatable to align at least the first elongate member with an access site of a patient.

8. The robotic instrument driver of claim 1, wherein the first and second pods are configured to be vertically and rotatably adjustable to optimize the insertion angle of the first elongate member into a patient.

9. The robotic instrument driver of claim 1, wherein the first and second pods are configured to be moveable vertically or rotatable about the respective first and second yaw axes in unison.

10. The robotic instrument driver of claim 1, wherein the second pod is movable independently from the first pod.

11. The robotic instrument driver of claim 10, wherein the first manipulation mechanism is of a type that is different from the second manipulation mechanism.

12. The robotic instrument driver of claim 10, further comprising a third manipulation mechanism, wherein the third manipulation mechanism is configured to insert or retract the first elongate member.

13. The robotic instrument driver of claim 10, wherein the first yaw axis is approximately orthogonal to an advancement axis along which at least the first pod is moveable.

14. The robotic instrument driver of claim 10, wherein the first pod and the second pod are both positioned on a rail, and the rail is attached to a bed.

15. The robotic instrument driver of claim 10, further comprising an anti-buckling device placed on or around the first elongate member.

16. The robotic instrument driver of claim 10, wherein the first and second pods are configured to be rotatable to align the first elongate member with an access site of a patient.

17. The robotic instrument driver of claim 10, wherein the first and second pods are configured to be vertically and rotatably adjustable to optimize the insertion angle of the first elongate member into a patient.

18. The robotic instrument driver of claim 10, wherein the first and second pods are configured to be movable vertically or rotatable about the respective first and second yaw axes in unison.

19. The robotic instrument driver of claim 10, wherein the second pod is movable independently from the first pod.

20. The robotic instrument driver of claim 1, wherein the first pod is configured to be movable vertically along the first yaw axis, wherein the second pod is configured to be movable vertically along the second yaw axis.

21. A system, comprising:
(a) a first pod comprising a first manipulation mechanism configured to advance or retract a second elongate member relative to a first elongate member, wherein the first pod is configured to be movable vertically, wherein the first pod is further configured to be rotatable about a first yaw axis; and
(b) a second pod comprising a second manipulation mechanism configured to advance or retract a third elongate member relative to the second elongate member, wherein the second pod is configured to be movable vertically, wherein the second pod is further configured to be rotatable about a second yaw axis.

22. The robotic instrument driver of claim 21, wherein the first pod is configured to be movable vertically along the first yaw axis, wherein the pod is configured to be movable vertically along the second yaw axis.

23. A method, comprising:
(a) articulating, via a first manipulation mechanism of a first pod, one or more steering wires in a first elongate member, the first pod further comprising a first active drive mechanism fixed relative to the first manipulation mechanism, the first active drive mechanism configured to insert or retract a second elongate member with respect to the first elongate member;
(b) articulating, via a second manipulation mechanism of a second pod, one or more steering wires in the second elongate member, the second pod further comprising a second active drive mechanism fixed relative to the second manipulation mechanism and configured to insert or retract a third elongate member with respect to the second elongate member; and
(c) moving the second pod independently from the first pod, wherein the first and second pod are each configured to be movable vertically, wherein the first and second pod are further each configured to be rotatable independently from each other to a respective yaw angle.

* * * * *